(12) United States Patent
Joplin et al.

(10) Patent No.: US 9,944,419 B2
(45) Date of Patent: Apr. 17, 2018

(54) SYSTEMS AND METHODS FOR A UNIT-OF-USE WRAP SEAL PACKING STATION

(71) Applicant: Express Scripts, Inc., St. Louis, MO (US)

(72) Inventors: Jonathan W. Joplin, Chesterfield, MO (US); Robert E. Hoffman, Linden, IN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 452 days.

(21) Appl. No.: 14/803,101

(22) Filed: Jul. 19, 2015

(65) Prior Publication Data

US 2016/0023790 A1    Jan. 28, 2016

Related U.S. Application Data (60) Provisional application No. 62/028,290, filed on Jul. 23, 2014.

(51) Int. Cl.
| | |
|---|---|
| *B65B 35/54* | (2006.01) |
| *B65B 57/14* | (2006.01) |
| *B65B 5/06* | (2006.01) |
| *B65B 35/24* | (2006.01) |
| *G06F 19/00* | (2018.01) |

(Continued)

(52) U.S. Cl.
CPC .............. *B65B 35/54* (2013.01); *B65B 5/067* (2013.01); *B65B 35/24* (2013.01); *B65B 57/14* (2013.01); *G06F 19/3456* (2013.01); *G06Q 10/08* (2013.01); *G07F 17/0092* (2013.01)

(58) Field of Classification Search
CPC ......... B65B 5/067; B65B 35/24; B65B 35/32; B65B 35/54; B65B 57/10; B65B 57/14; B65G 1/1376; B65G 1/1378; G06Q 10/08; G06Q 10/087; G07F 17/0092; G06F 19/3456; G06F 19/3462
USPC .................. 53/52, 54, 55, 58, 154, 237, 251
See application file for complete search history.

(56) References Cited

U.S. PATENT DOCUMENTS 3,058,272 A * 10/1962 Huber ..................... B65B 61/28
                                                       53/251
4,534,156 A *  8/1985 Smith ..................... B65B 57/14
                                                       141/176

(Continued)

FOREIGN PATENT DOCUMENTS

| DE | 29722872 U1 * | 4/1998 | ........... B65G 1/1376 |
| DE | 102004017579 A1 * | 11/2005 | ........... B65G 1/1376 |

(Continued)

*Primary Examiner* — Stephen F Gerrity
(74) *Attorney, Agent, or Firm* — Husch Blackwell LLP (57) ABSTRACT

A system comprising a staging area and a packing area. The staging area may include a plurality of staging bins and a shuttle moveable along the plurality of staging bins. A staging bin of the plurality of staging bins may be configured to selectively retain a component of an order therein. Such staging bin may be configured to selectively release the component to the shuttle. The packing area may include a slide, a scanner, and a wrap seal conveyor. The shuttle may be configured to release the component onto the slide, and the scanner may be operable to scan and verify the component during placement of the component onto the wrap seal conveyor.

22 Claims, 8 Drawing Sheets

(51) Int. Cl.
*G06Q 10/08* (2012.01)
*G07F 17/00* (2006.01)

(56) References Cited

U.S. PATENT DOCUMENTS

| | | | | |
|---|---|---|---|---|
| 4,542,808 | A * | 9/1985 | Lloyd, Jr. et al. | ... B65G 1/1376 186/56 |
| 4,870,799 | A * | 10/1989 | Bergerioux et al. | . B65G 1/1376 221/123 |
| 4,971,513 | A * | 11/1990 | Bergerioux et al. | . B65G 1/1376 414/285 |
| 5,005,338 | A * | 4/1991 | Kemkers et al. | ....... B65B 15/04 53/54 |
| 5,267,426 | A * | 12/1993 | Davis | ...................... B65B 35/54 53/154 |
| 5,604,692 | A * | 2/1997 | Yuyama | ................. A61J 7/0069 700/240 |
| 5,720,154 | A * | 2/1998 | Lasher et al. | ....... G07F 17/0092 53/168 |
| 6,170,230 | B1 * | 1/2001 | Chudy et al. | ....... G07F 17/0092 53/168 |
| 6,208,908 | B1 * | 3/2001 | Boyd et al. | .......... G06Q 10/087 198/349 |
| 6,370,841 | B1 * | 4/2002 | Chudy et al. | ....... G07F 17/0092 221/10 |
| 6,681,549 | B1 * | 1/2004 | Zhao et al. | ............. A61K 9/009 53/443 |
| 6,769,228 | B1 | 8/2004 | Mahar | |
| 6,892,512 | B2 | 5/2005 | Rice et al. | |
| 7,010,899 | B2 | 3/2006 | McErlean et al. | |
| 7,398,134 | B2 * | 7/2008 | Carley et al. | ............. B07C 5/38 414/788.1 |
| 7,455,169 | B2 * | 11/2008 | Schafer | ................... B65B 5/101 198/369.2 |
| 8,991,138 | B2 * | 3/2015 | Yuyama et al. | .... G07F 17/0092 53/235 |
| 9,701,474 | B2 * | 7/2017 | Hellenbrand | ........ B65G 1/1376 |
| 2004/0040975 | A1 * | 3/2004 | Hunter et al. | ....... B65G 1/1378 221/92 |
| 2004/0065053 | A1 * | 4/2004 | Rice et al. | .......... G06F 19/3462 53/445 |
| 2006/0051186 | A1 * | 3/2006 | Maldina et al. | ........ B65B 35/32 414/268 |
| 2007/0157579 | A1 * | 7/2007 | Basque et al. | .......... B65B 5/067 53/495 |
| 2011/0067781 | A1 * | 3/2011 | Osborne | .......... G07F 17/0092 141/37 |
| 2012/0228083 | A1 * | 9/2012 | Terzini | .................... G07F 11/62 198/345.1 |
| 2014/0025545 | A1 * | 1/2014 | Carson et al. | ...... G06F 19/3462 705/29 |
| 2015/0191261 | A1 * | 7/2015 | Clark et al. | ............. B65B 35/32 53/443 |

FOREIGN PATENT DOCUMENTS

| | | | | |
|---|---|---|---|---|
| DE | 102012025163 | A1 * | 6/2014 | ........... B65G 1/1378 |
| EP | 0010686 | A1 * | 5/1980 | ............. B65B 21/04 |
| WO | WO 2012147261 | A1 * | 11/2012 | ........... B65G 1/1378 |

* cited by examiner

SYSTEMS AND METHODS FOR A UNIT-OF-USE WRAP SEAL PACKING STATION

CROSS-REFERENCE TO RELATED APPLICATION

This application claims priority to U.S. Provisional Patent Application No. 62/028,290, filed Jul. 23, 2014, the entirety of which is hereby incorporated by reference.

FIELD

The present application relates generally to the technical field of automated filling centers. In a specific example, the present application may relate to a high volume fulfillment center, e.g., a high volume pharmacy and to systems and devices used in filling prescriptions and prescription orders at a high volume pharmacy.

BACKGROUND

A high-volume pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

DETAILED DESCRIPTION

Example systems and methods for a unit-of-use wrap seal packing station (e.g., in a pharmacy) are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a high volume pharmacy. The prescription order may include more than one prescription drug for fulfillment. Each prescription drug in a prescription order is an order component of the prescription order. Generally, the order components are pill bottles or other containers and packaging having a quantity of a prescription drug therein.

The prescription drugs may be dispensed at various sections of the high volume pharmacy. Some prescription orders may require manual fulfillment of order components. Distribution of order components necessitating manual fulfillment is provided by a distribution section and one or more the one manual sections. In general, manual handling includes manual fulfillment of prescription drugs (e.g., by a pharmacist utilizing or directly controlling certain equipment). Manual handling occurs at one or more than one manual sections, from which the order component exits the manual fulfillment device. Some prescription orders or portions of prescription orders may be filled using automated machines, which can fill prescription orders at a greater rate than manual fulfillment. Other prescriptions may be filled with unit of use products.

Figure 1:
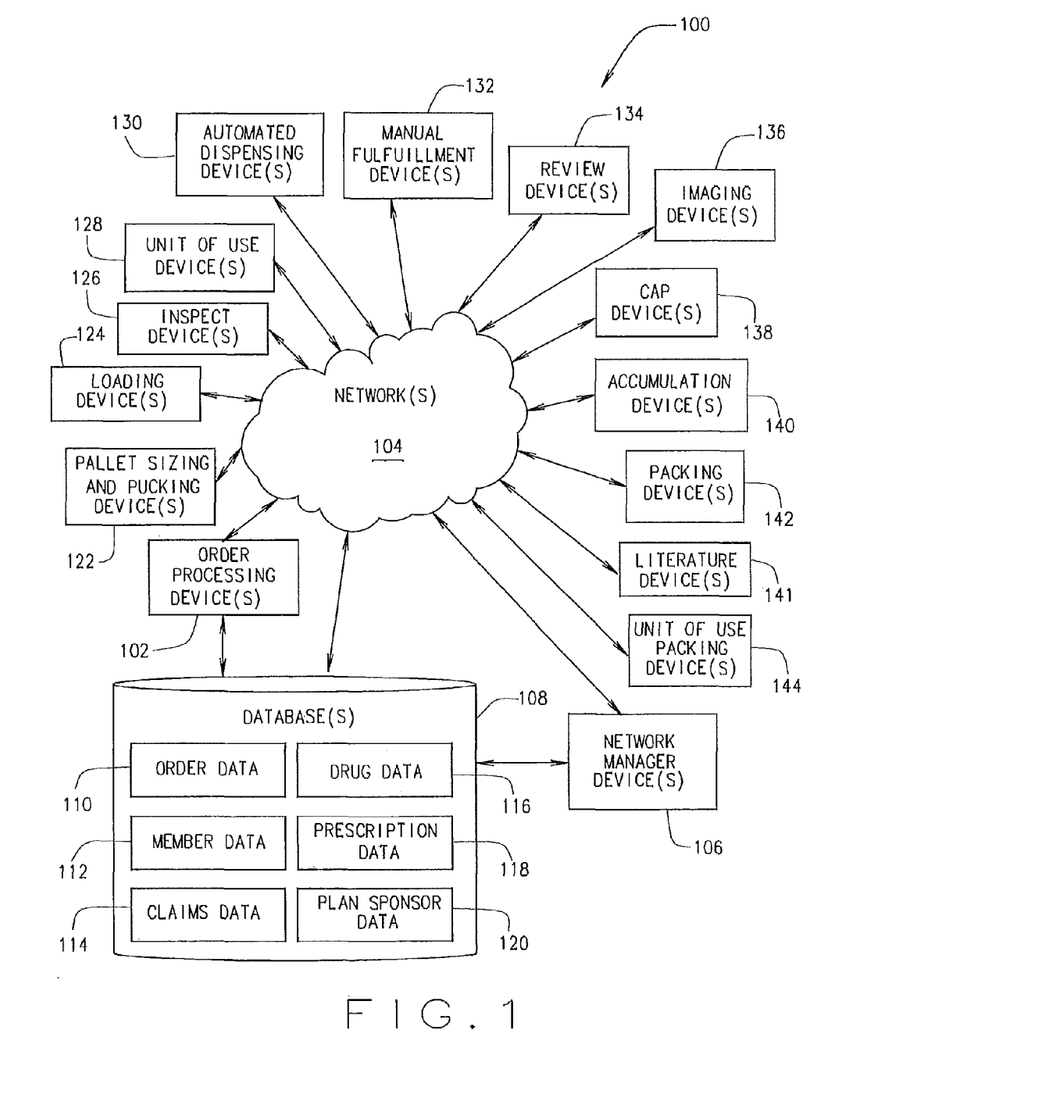
FIG. 1 is a block diagram of an example system, according to an example embodiment.

FIG. 1 is a block diagram of an example system 100, according to an example embodiment. While the system 100 is generally described as being deployed in a high volume pharmacy (e.g., a mail order pharmacy, a direct delivery pharmacy, an automated pharmacy, and the like), the system 100 may otherwise be deployed. The system 100 may include an order processing device 102 in communication with a benefit manager device 106 over a network 104. Additional devices which may be in communication with the benefit manager device 106 and/or the order processing device 102 over network 104 include: database(s) 108 which may store one or more than one of order data 110, member data 112, claims data 114, drug data 116, prescription data 118, and plan sponsor data 120; pallet sizing and pucking device(s) 122; loading device(s) 124; inspect device(s) 126; unit of use device(s) 128; automated dispensing device(s) 130; manual fulfillment device(s) 132; review device(s) 134; imaging device(s) 136; cap device(s) 138; accumulation device(s) 140; literature device(s) 141; packing device(s) 142; and unit of use packing device(s) 144. The system 100 may also include additional devices, which may communicate with each other over network 104 or directly.

The order processing device 102 may receive information about prescriptions being filled at a pharmacy in which the order processing device 102 is deployed. In general, the order processing device 102 is a device located within or otherwise associated with a pharmacy location to enable fulfillment of a prescription by dispensing prescription drugs. In some embodiments, the order processing device 102 may be a device separate from a pharmacy that enables communication with other devices located within a pharmacy. For example, the order processing device 102 may be in communication with another order processing device 102 and/or other devices 122-144 located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a prescription order as it is fulfilled. A prescription order may include one or more than one prescription to be filled by the pharmacy. The order processing device 102 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 102 may operate on its own or in combination with the benefit manager device 106. The order processing device 102 may track and/or schedule the literature or other paperwork associated with each order or multiple prescription orders that are being shipped together.

Examples of the devices 102, 106 include a set-top box (STB), a receiver card, a mobile telephone, a personal digital assistant (PDA), a display device, a portable gaming unit, a tablet, and a computing system; however other devices may also be used. For example, the devices 102, 106 may include a mobile electronic device, such an IPHONE or IPAD device by Apple, Inc., mobile electronic devices powered by ANDROID by Google, Inc., and a BLACKBERRY device by Blackberry Limited. The order processing device 102 may also include other computing devices, such as desktop computing devices, notebook computing devices, netbook computing devices, gaming devices, servers, and the like. The device 102 may include circuitry, a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for creation and/or management of the pharmacy or drug benefit. While this benefit manager operating the benefit manager device 106 is typically a pharmacy benefit manager (PBM), other entities may operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, or otherwise.

Some of the operations of the PBM that operates the benefit manager device 106 may include the following. A member (or a person on behalf of the member) of a pharmacy benefit plan administered by or through the PBM attempts to obtain a prescription drug at a retail pharmacy location where the member can obtain drugs in a physical store from a pharmacist or pharmacist technician, or in some instances through mail order drug delivery from a mail order pharmacy location. The member may also obtain a prescription drug directly or indirectly through the use of a machine, such as a kiosk, vending unit, mobile electronic device, or a different type of mechanical, electrical, electronic communication device and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of a plan sponsor or client with the PBM. The member's co-pay may be based on a flat co-pay (e.g., $10), co-insurance (e.g., 10%), and/or a deductible (e.g., for first $500 of annual prescription drug spend) for certain prescription drugs, certain types and/or classes of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. The co-pay may also vary based on the delivery channel used to receive the prescription drug. For example, the co-pay for receiving prescription drug from a mail order pharmacy location may be less than the co-pay for receiving prescription drug from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing an applicable formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 106 and/or an additional device.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage or peer-to-peer connection(s)) and/or through the network 104 (e.g., in a cloud configuration or software as a service) with a database 108 (e.g., as may be retained in memory or otherwise). The database 108 may be deployed on the order processing device 102, the benefit manager device 106, on another device of the system 100, or otherwise. The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials and/or the type and/or size of container in which the drug is or is preferably dispensed. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high volume fulfillment center to fulfill a pharmacy order.

In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the prescription container (e.g., a prescription bottle and sealing lid) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets used to transport prescriptions within the pharmacy may also be stored as order data 110.

The member data 112 includes information regarding the members associated with the benefit manager. The information stored as member data 112 may include personal information, personal health information, protected health information, and the like. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, e.g., the high volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data 112, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of the devices 122-144, recited above. In some embodiments, operations performed by one of these devices 122-144 may be performed sequentially, or in parallel with the operations of another device as may be coordinated by the order processing device 102. In some embodiments, the order processing device 102 tracks a prescription with the pharmacy based on operations performed by one or more of the devices 122-144.

In some embodiments, the system 100 may transport prescription drug containers (e.g., between one or more than one of the devices 122-144 in the high volume fulfillment center) by use of pallets. The pallet sizing and pucking device 122 may configure pucks in a pallet. A pallet may be a transport structure for a number of prescription containers, and may include a number of cavities. A puck may be placed in one or more than one of the cavities in a pallet by the pallet sizing and pucking device 122. A puck may include a receptacle sized and shaped to receive a prescription container. Such containers may be supported by the pucks during carriage in the pallet and during movement through the fulfillment process. Different pucks may have differently sized and shaped receptacles to accommodate containers of differing sizes, as may be appropriate for different prescriptions. Pucks allow the standardization of equipment engaging differently sized drug containers such that some automated equipment can move the drug container by gripping the puck that is supporting the container and allow the use of a standardized pallet that holds a plurality of pucks have a same outer dimension while having differently sized receptacles therein to hold differently sized drug containers. The pucks may also operate to ensure that a drug container is centered in a location on the pallet.

The arrangement of pucks in a pallet may be determined by the order processing device 102 based on prescriptions which the order processing device 102 decides to launch. In general, prescription orders in the order database 110 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet.

The loading device 124 may load prescription containers into the pucks on a pallet by a robotic arm, a pick and place mechanism, or the like. In one embodiment, the loading device 108 has robotic arms or pickers to grasp a prescription container and move it to and from a pallet. The loading device 124 may also print a label which is appropriate for a container that is to be loaded onto the pallet, and apply the label to the container. The pallet may be located on a conveyor assembly during these operations. In an example embodiments, the drug containers may be positioned in the pucks by the loading device 124 prior to the pucks being placed in the pallet.

The inspect device 126 may verify that containers in a pallet are correctly labeled and in the correct spot on the pallet. The inspect device 126 may scan the label on one or more than one container on the pallet. Labels of containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit of use device 128 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like. Prescription drug products dispensed by the unit of use device 128 may be packaged individually or collectively for shipping, or may be shipped in combination with other prescription drugs dispensed by other devices in the high volume fulfillment center.

The automated dispensing device 130 may include one or more than one devices that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack. Prescription drugs dispensed by the automated dispensing devices 130 may be packaged individually or collectively for shipping, or may be shipped in combination with other prescription drugs dispenses by other devices in the high volume fulfillment center.

The manual fulfillment device 132 may provide for manual fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100. In an example embodiment, the container may be joined with other containers in a prescription order for a patient or member, e.g., on a pallet or at the accumulation device 140. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review can be performed at the manual station.

The imaging device 136 may image containers once they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap or otherwise associate a message into the cap, although this process may be performed by a subsequent device in the high volume fulfillment center.

The accumulation device 140 accumulates various containers of prescription drugs in a prescription order. The accumulation device 140 may accumulate prescription containers from various devices or areas of the pharmacy. For example, the accumulation device 140 may accumulate prescription containers from the unit of use device 128, the automated dispensing device 130, the manual fulfillment device 132, and the review device 134, at the high volume fulfillment center. The accumulation device 140 may be used to group the prescription containers prior to shipment to the member or otherwise.

In some embodiments, the literature device 141 folds or otherwise prepares the literature for inclusion with a prescription drug order (e.g., in a shipping container). In some embodiments, the literature device 141 that prints the literature may be separate from the literature device that prepares the literature for inclusion with a prescription order.

The packing device 142 packages a prescription order in preparation for shipping the order. The packing device 142 may box, bag, or otherwise package the fulfilled prescription order for delivery. The packing device 142 may further place inserts, e.g., literature or other papers, into the packaging received from the literature device 141 or otherwise. For example, bulk prescription orders may be shipped in a box, while other prescription orders may be shipped in a bag which may be a wrap seal bag. The packing device 142 may label the box or bag with the address and a recipient's name. The label may be printed and affixed to the bag or box, be printed directly onto the bag or box, or otherwise associated with the bag or box. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The ultimate package may then be shipped through postal mail, through a mail order delivery service that ships via group and/or air (e.g., UPS, FEDEX, or DHL), through delivery service, through a local delivery service (e.g., a courier service), through a locker box at a shipping site (e.g., an AMAZON locker or a post office box), or otherwise.

The unit of use packing device 144 packages a unit of use prescription order in preparation for shipping the order. The unit of use packing device 144 may include manual scanning of containers to be bagged for shipping to verify each container in the order. In an example embodiment, the manual scanning may be performed at a manual station.

While the system 100 in FIG. 1 is shown to include single devices 102, 106, 122-144 multiple devices may be used. The devices 102, 106, 122-144 may be the same type or model of device or may be different device types or models. When multiple devices are present, the multiple devices may be of the same device type or models or may be a different device type or model. The types of devices 102, 106, 122-144 shown in FIG. 1 are example devices. In other configurations of the system 100, lesser, additional, or different types of devices may be included.

Moreover, the system 100 shows a single network 104; however, multiple networks can be used. The multiple networks may communicate in series with each other to link the devices 102, 106, 122-144 or in parallel to link the devices 102, 106, 122-144. Multiple devices may share processing and/or memory resources. The devices 102, 106, 122-144 may be located in the same area or in different locations. For example, the devices 102, 106, 122-144 may be located in a building or set of adjoining buildings. The devices 102, 106, 122-144 may be interconnected (e.g. by conveyors), networked, and/or otherwise in contact with one another or integrated with one another, e.g., at the high volume fulfillment center. In addition, the functionality of a device may be split among a number of discrete devices and/or combined with other devices.

The system 100 may include a single database, or multiple databases, maintained by respective devices operated by or on behalf one or a number of different persons and/or organizations. The communication may occur directly (e.g., through local storage) and/or through the network 104 (e.g., in a cloud configuration or software-as-a-service) with a device that stores a respective database.

Figure 2:
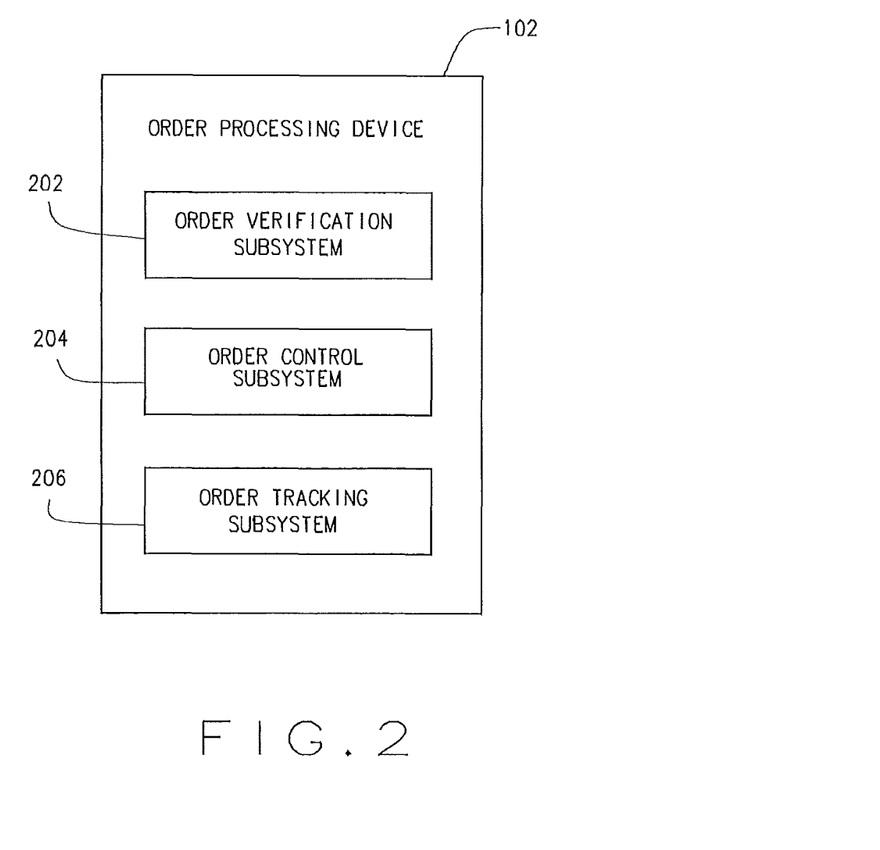
FIG. 2 is a block diagram of an example order processing device that may be deployed within the system of FIG. 1, according to an example embodiment.

FIG. 2 illustrates the order processing device 102, according to an example embodiment. The order processing device 102 may be used by one or more than one operator to generate prescription orders, make routing decisions, make prescription order consolidation decisions, track literature within the system 100, and/or view order status and other order related information. For example, the prescription order may be comprised of order components. The order processing device 102 may receive instructions to fulfill an order without operator intervention. An order component may include a prescription drug fulfilled by use of a container through the system 100. The order processing device 102 may direct an order component to the manual fulfillment device 132 and/or to the review device 134, and direct other components to the automated dispensing device 130. The order processing device 102 may direct order components to the accumulation device 140 for aggregation before shipping. The order processing device 102 may direct the order components directly to the packing device 142 if the prescription order does not require accumulation from various areas of the pharmacy for completion. The order processing device 102 may be deployed in the system 100, or may otherwise be used.

The order processing device 102 may include an order verification subsystem 202, an order control subsystem 204, and/or an order tracking subsystem 206. Other subsystems may also be included in the order processing device 102.

The order verification subsystem 202 may communicate with the benefit manager device 106 to, verify the eligibility of the member, review the formulary to determine appropriate co-pay, coinsurance, and deductible for the prescription drug, and/or perform a DUR. Other communications between the order verification subsystem 202 and the benefit manager device 106 may be performed for a variety of purposes.

The order control subsystem 204 controls various movements of the containers and/or pallets along with various filling functions during their progression through the system 100.

In some embodiments, the order control subsystem 204 may identify the prescribed drug in one or more than one prescription order as capable of being fulfilled by the automated dispensing device 130. The order control subsystem 204 may determine which prescriptions are to be launched, and may determine that a pallet of automated-fill containers is to be launched. The order control subsystem 204 may determine that an automated-fill prescription of a specific pharmaceutical is to be launched, and may examine a queue of orders awaiting fulfillment for other prescription orders which will be filled with the same pharmaceutical. The order control subsystem 204 may then launch orders with similar automated-fill pharmaceutical needs together in a pallet to the automated dispensing device 130.

In some embodiments, the order control subsystem 204 may identify the prescribed drug in one or more than one prescription order as needing to be fulfilled manually and may direct the container or order component to the manual fulfillment device 132 to achieve the manual fulfillment. The order control subsystem 204 may determine which prescriptions are to be launched, and may determine that a pallet of manual-fill containers is to be launched. The order control subsystem 204 may determine that a manual-fill prescription of a specific pharmaceutical is to be launched, and may examine a queue of orders awaiting fulfillment for other prescription orders which will be filled with the same pharmaceutical. The order control subsystem 204 may then launch orders with similar manual-fill pharmaceutical needs together in a pallet to the manual fulfillment device 132. As the devices 122-144 may be interconnected by a system of conveyors or other container movement systems, the order control subsystem 204 may control various conveyors to deliver the pallet from the loading device 124 to the manual fulfillment device 132, for example.

In some embodiments, the order control subsystem 204 may identify the container as a unit-of-use container, and may direct the unit-of-use container and/or other components in that order to the unit-of-use packing device 144 for packing. The devices 122-144 may be interconnected by a system of conveyors or other container movement systems. Thus, the order control subsystem 204 may control various conveyors to deliver a unit-of-use container and/or other components in that order to the unit-of-use packing device 144.

The order tracking subsystem 206 may track a prescription order as it progresses (or stops) toward fulfillment. The order tracking subsystem 206 may track, record and/or update order history, order status, or the like. The order tracking subsystem 206 may store data locally (e.g., in a memory) or as a portion of the order data 110 stored in the database 108.

Figure 3A:
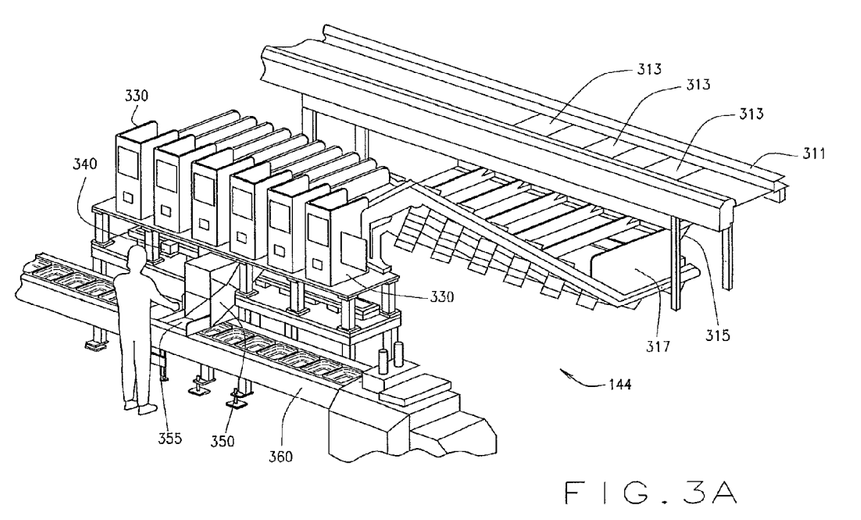
FIG. 3A is a schematic perspective view of a unit-of-use packing device that may be deployed within the system of FIG. 1, according to an example embodiment.
Figure 3B:
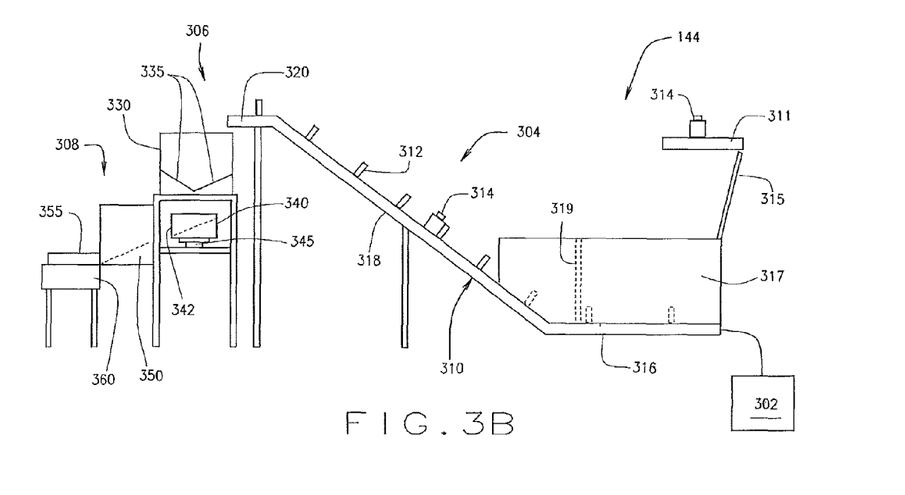
FIG. 3B is a side elevation view of a unit-of-use packing device that may be deployed within the system of FIG. 1, according to an example embodiment.

FIGS. 3A and 3B illustrate a unit-of-use packing device 144, according to an example embodiment. The unit-of-use packing device 144 may be deployed in the system 100, or may otherwise be deployed. A unit-of-use wrap seal packaging center 300 of a pharmacy may be deployed within the unit-of-use packing device 144, or may be otherwise deployed. A unit-of-use wrap seal packaging center 300 may be operated by one or more than one pharmacists and/or pharmacist technicians to package unit-of-use prescription orders for shipment.

The unit-of-use packing device 144 may include a control unit 302, a conveyor section 304, a staging area 306, and a packing area 308. The control unit 302 may operate at the direction of the order processing device 102. As shown in FIG. 3B, the control unit 302 is shown in block form. However, it will be understood that the control unit 302 is operatively associated with and connected to unit-of-use packing device 144.

The conveyor section 304 may include a staging conveyor 310. A single staging conveyor 310 or multiple staging conveyors 310 may be used. In some embodiments, a staging conveyor 310 may be a Z conveyor. An inclined conveyor or any other suitable mechanism may be used instead of or in addition to a Z conveyor. While FIG. 3A depicts six staging conveyors 310, a greater or lesser number of conveying mechanisms may be used.

The staging conveyor 310 may include cleats 312 to assist containers 314 move along the staging conveyor 310. The cleats 312 may be constructed of rubber, PVC, or of other materials and spaced uniformly or otherwise. The staging conveyor 310 may include a lower horizontal section 316, an inclined section 318, and an upper horizontal section 320. The conveyor section 304 may also include a feed conveyor 311 which brings the containers 314 to the unit-of-use packing device 144. The feed conveyor 311 may include one or more than one drop door 313 which may be a bomb bay style drop door. Each staging conveyor 310 may be associated with its own drop door 313, such that the drop door 313 drops the container 314 down a chute 315 and into a holding bin 317 associated with that staging conveyor 310. Additionally, each holding bin 317 may include a door 319 (shown in phantom in FIG. 3B) which may open to allow a container 314 to ride the staging conveyor 310 out of the holding bin 317 as appropriate. The staging conveyor 310 conveys one or more than one container 314 which may be components of a prescription order from the lower horizontal section 316, and up the inclined section 318 to the upper horizontal section 320. The upper horizontal section 320 of the staging conveyor 310 leads to the staging area 306.

The staging area 306 may include a staging bin 330. A single staging big 330 or multiple staging bins 330 may be used. In some embodiments, each staging conveyor 310 is associated with its own staging bin 330. The containers 314 which form a prescription order are carried by the staging conveyor 310 to the staging bin 330, and may be deposited within the staging bin 330. The staging bin 330 may include one of more than one door 335 which, when closed, hold the containers 314 within the staging bin 330. The doors 335 may open to drop any containers 314 contained within the staging bin 330 out of the staging bin 330. In some embodiments, other structures may be used to selectively retain the containers 314 within the staging bin 330 in place of the doors 335.

The staging area 306 may also include a shuttle 340 which moves along a track 345. The track 345 may extend beneath each of the staging bins 330, so as to allow the shuttle 340 to move beneath the staging bins 330. The track 345 may be positioned below the staging bins 330 to allow the shuttle 340 to be positionable beneath the doors 335 such that the shuttle 340 receives any of the containers 314 housed within the staging bin 330 when the doors 335 of that staging bin 330 are opened. In some embodiments, the shuttle 340 and the track 345 may be positioned elsewhere rather than directly beneath the staging bins 330, such as when a structure other than the doors 335 is used to selectively retain and release the containers 314 from the staging bins 330. For example, if a structure which allows the containers 314 to exit from one side of the staging bin 330 rather than through the bottom of the staging bin 330 is used, the track 345 and the shuttle 340 may be positioned proximate the staging bins 330. The shuttle 340 may be controllable by the control unit 302.

The packing area 308 may include a slide 350, a wrap seal conveyor 360, and a pre-scan gathering area 355 which may be positioned generally above the wrap seal conveyor 360 and at the bottom of the slide 350. As can be best seen in FIG. 4, the packing area 308 may also include a scanner 357 which may be a manual scanner. In an example embodiment, the scanner 357 may be a secured overhead high speed camera or scanner 357, although it will be recognized that an undermounted scanner 357 may instead or also be used. An operator manually passes a container 314 across the scanner 357 to scan the container 314. The wrap seal conveyor 360 may include wrap seal pockets 365 into which the containers 314 may be placed for sealing and shipping.

Figure 4:
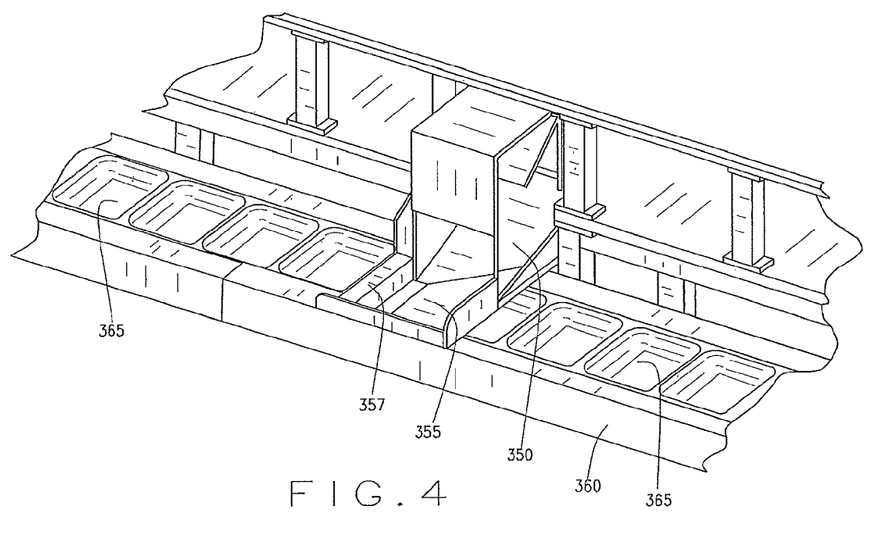
FIG. 4 is an enlarged perspective schematic view of a staging area of the unit-of-use packing device of FIGS. 3A and 3B according to an example embodiment.

Once the shuttle 340 receives one or more than one container 314 from the staging bin 330, it may move to a position proximate the slide 350. The shuttle 340 may then release the containers 314 via the door 342 so as to allow the containers 314 to slide down the slide 350 and into the pre-scan gathering area 355. As the containers 314 land in the pre-scan gathering area 355, a worker may pick up each container 314 and scan the container 314 via the scanner 357 before placing the container 314 into a wrap seal pocket 365 on a wrap seal conveyor 360. A wrap seal pocket 365 may be a flexible mailer bag which may be pre-formed. In some embodiments, the wrap seal pocket 365 may be a portion of a flexible mailer bag, into which containers 314 are placed, after which the wrap seal pocket 365 is covered and sealed.

The staging area 306 may, in some embodiments, include an exception zone for the containers 314 which are determined to be an exception. An exception determination may occur during scanning of the containers 314 at the scanner 357, while the containers 314 reside in the staging bin 330, after the containers 314 have been dropped by the staging bins 330 to the shuttle 340, or at any location in unit-of-use wrap seal packaging center 300 in which the containers 314 may be imaged, or scanned, and/or viewed. A worker may make the exception determination based on the scan, and may physically place the container 314 in the exception zone. In some embodiments, the shuttle 340 may take the container 314 to the exception zone. The exception zone may be a separate bin, or a tote, or a conveyor which takes the containers 314 deemed exceptions to, for example, the review device 134.

Figure 5:
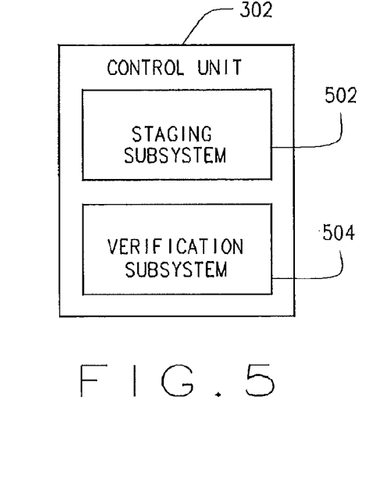
FIG. 5 is a block diagram of a control unit that may be deployed within the unit-of-use packing device of FIGS. 3A, 3B and 4, according to an example embodiment.

FIG. 5 illustrates a control unit 302, according to an example embodiment. The control unit 302 may be deployed in the unit-of-use wrap seal packaging center 300, or may otherwise be deployed. The control unit 302 may be communicatively connected to one or more than one components in the conveyor section 304, the staging area 306, and/or the packing area 308, such as the staging bins 330, the shuttle 340, the scanner 357, and the like. The control unit 302 may include a staging subsystem 502 and a verification subsystem 504. The staging subsystem 502 may enable the control unit 302 to stage a single container 314 or multiple containers 314 which make up a prescription order in the shuttle 340 while a previous prescription order is being acted upon by a worker in the packing area 308. The verification subsystem 504 may enable the control unit 302 to determine whether the container 314 or containers 314 scanned by the worker via the scanner 357 are the correct containers 314 are ready for shipping.

Figure 6:
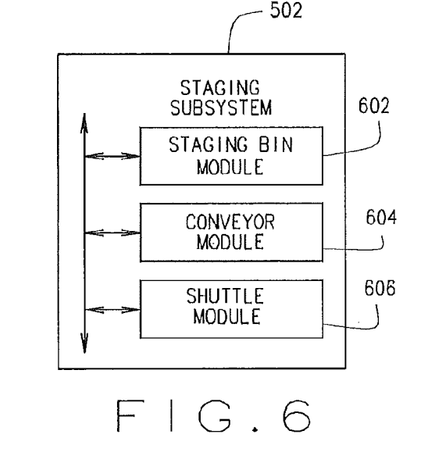
FIG. 6 is a block diagram of a staging subsystem that may be deployed within the control unit of FIG. 5, according to an example embodiment.

FIG. 6 illustrates an example staging subsystem 502 that may be deployed in the control unit 302, or may be otherwise deployed in another system. One or more modules are communicatively coupled and included in the staging subsystem 502 to enable the staging subsystem 502 to stage prescription orders. The modules of the staging subsystem 502 that may be included are a staging bin module 602, a conveyor module 604 and/or a shuttle module 606. Other modules may also be included.

In some embodiments, the modules of the staging subsystem 502 may be distributed so that some of the modules are deployed in other devices within the system 100. In one embodiment, the modules are deployed in memory and executed by a processor coupled to the memory. The functionality contained within the modules 602-606 may be combined into a lesser number of modules, further divided among a greater number of modules, or redistributed among existing modules. Other configurations including the functionality of the modules 602-606 may be used.

The staging bin module 602 may instruct a selected staging bin 330 to open or close its doors 335. The conveyor module 604 may instruct the staging conveyor 310 associated with an empty staging bin 330 to advance and deposit the next prescription order of one or more than one containers 314 into that staging bin 330. The shuttle module 606 may instruct the shuttle 340 to move beneath a selected staging bin 330. In some embodiments, the shuttle module 606 may also instruct the shuttle 340 to move to the slide 350 and release a prescription order of one or more than one containers 314 onto the slide 350.

Figure 7:
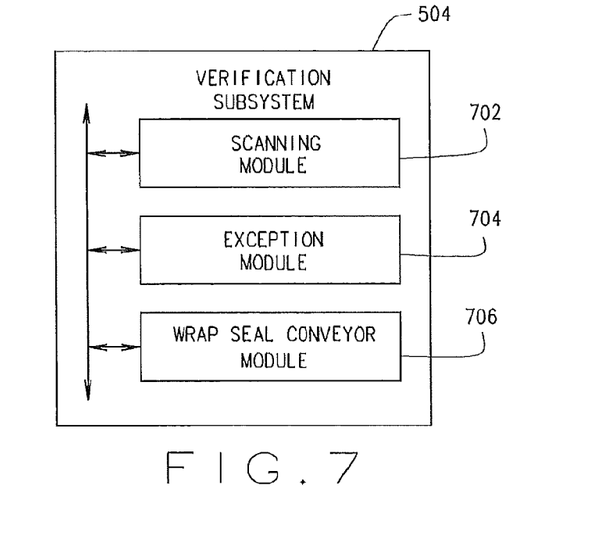
FIG. 7 is a block diagram of verification subsystem that may be deployed within the control unit of FIG. 5, according to an example embodiment.

FIG. 7 illustrates an example verification subsystem 504 that may be deployed in the control unit 302, or may be otherwise deployed in another system. One or more modules are communicatively coupled and included in the verification subsystem 502 to enable the verification subsystem 504 to verify prescription orders. The modules of the verification subsystem 504 that may be included are a scanning module 702, an exception module 704, and/or a wrap seal conveyor module 706. Other modules may also be included.

In some embodiments, the modules of the verification subsystem 504 may be distributed so that some of the modules are deployed in other devices within the system 100. In one embodiment, the modules are deployed in memory and executed by a processor coupled to the memory. The functionality contained within the modules 702-706 may be combined into a lesser number of modules, further divided among a greater number of modules, or redistributed among existing modules. Other configurations including the functionality of the modules 702-706 may be used.

The scanning module 702 may communicate with the scanner 357 to receive the result of the scan of the container 314. The exception module 704 may determine whether an exception has occurred. In one embodiment, if the container 314 which does not belong in the present prescription order is detected in the scan, or if not all of the containers 314 which should be present for the given prescription order are scanned, the exception module 704 may determine that an exception has occurred. The exception module 704 may alert a worker to the exception via a visual or auditory alert, or the like. Alternatively, the worker may be responsible for determining when an exception has occurred. The wrap seal conveyor module 706 may instruct the wrap seal conveyor 360 to advance when no exceptions are found by the exception module 704.

Figure 8:
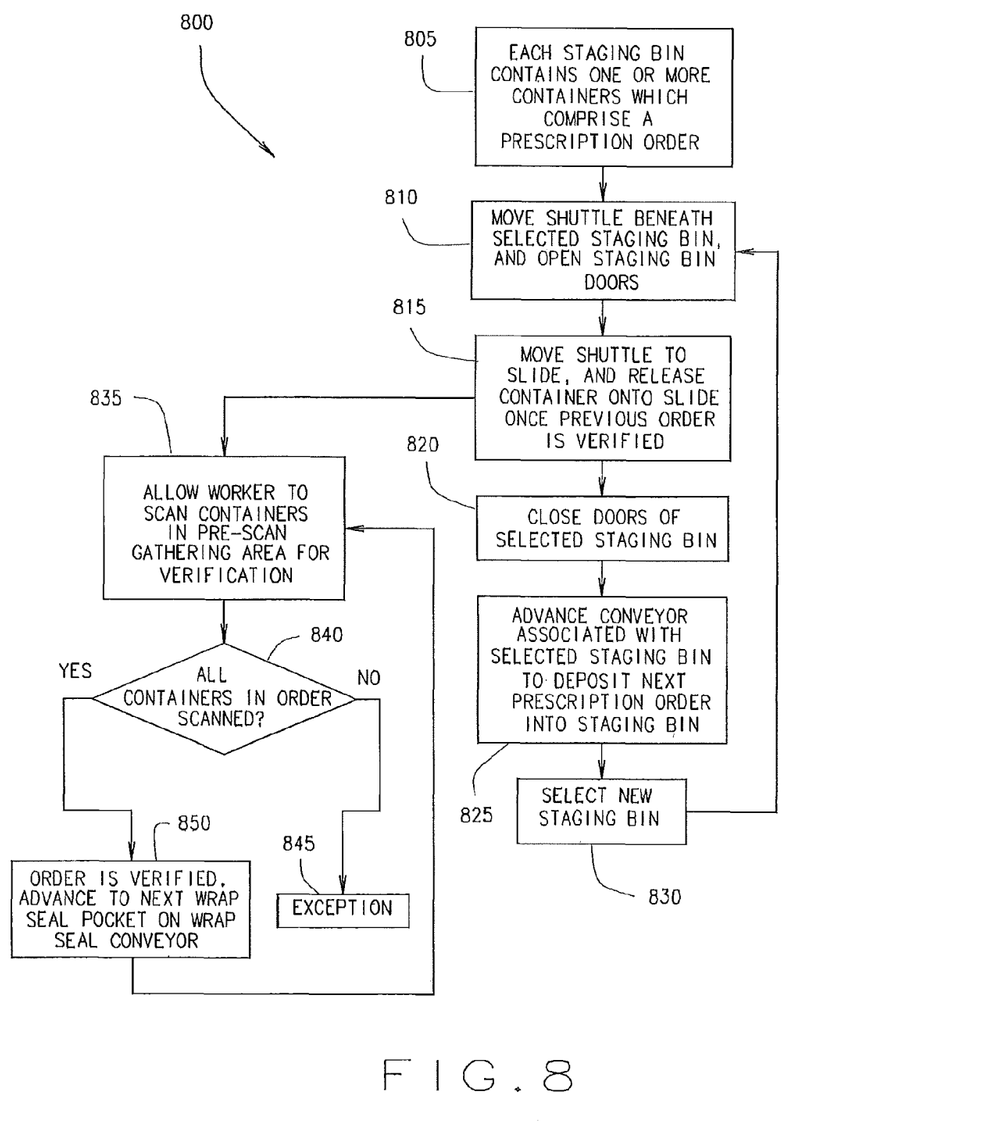
FIG. 8 is an example process flow illustrating a method of unit-of-use packing, according to an example embodiment.

FIG. 8 illustrates a method 800 for wrap seal unit-of-use packaging, according to an example embodiment. The method 800 may be performed by the unit-of-use packing device 144 as instructed by the control unit 302, or may be otherwise performed.

At block 805, it is assumed that each staging bin 330 already contains one or more than one container 314 which comprise a prescription order. At block 810, the shuttle 340 may be moved to a position beneath the selected staging bin 330, and the doors 335 of the selected staging bin 330 may be opened to drop the containers 314 from that staging bin 330 to the shuttle 340. At block 815, the shuttle 340 may be moved adjacent to the slide 350. If a worker is still handling a previous prescription order, the shuttle 340 may wait to drop its containers 314 onto the slide 350 until the previous prescription order has been verified by the worker. The shuttle 340 may then release the containers 314 onto the slide 350. At block 820, the doors 335 of the selected staging bin 330 may be closed, and at block 825, the staging conveyor 310 associated with the selecting staging bin 330 may be advanced to deposit the next prescription order of the containers 314 into the selected staging bin 330. At block 830, a new staging bin 330 may be selected, which may or may not be the same as the previously selected staging bin 330. Once the new staging bin 330 is selected, the process may revert back to block 810 in which the shuttle 340 may be moved to a position below the newly selected staging bin 330 and the process repeats.

In some embodiments, after performing operations at block 815 in which the shuttle 340 may release its containers 314 onto the slide 350 once the previous prescription order has been verified by the worker, the process 800 may advance to block 835 in which the containers 314 have slid down slide 350 and have gathered in the pre-scan gathering area 355. A worker may scan each container 314 in the prescription order via the scanner 357. At decision block 840, a determination may be made as to whether all of the containers 314 in a prescription order have been scanned and are accounted for. Such determination may be made by a worker who scans the containers 314 in some embodiments, and by the control unit 302 in other embodiments. If not, at block 845, the order may be deemed an exception. In an example embodiment, an order may also be deemed an exception if product literature associated with the order is missing, incomplete, incorrect or the like. If all containers 314 in the prescription order are scanned and are account for, the order may then be verified at block 350, and the containers 314 may be placed in a wrap seal pocket 365. The wrap seal conveyor 360 may then be advanced, and the method 800 may revert back to block 835 after the shuttle 340 has released the next prescription order of the containers 314 onto the slide 350 as per block 815.

In some embodiments, process steps 805-830 may occur simultaneously with process steps 835-850. As a non-limiting example, once one or more containers 314 have been transported to the pre-scan gathering area 355 and the worker begins scanning such containers 314, the shuttle 340 may have already moved to a position below another staging bin 330 to receive another prescription order and continue the process. By pre-staging the next prescription order as the worker is actively verifying the previous prescription order, the process 800 may result in more efficient unit-of-use packing.

Figure 9:
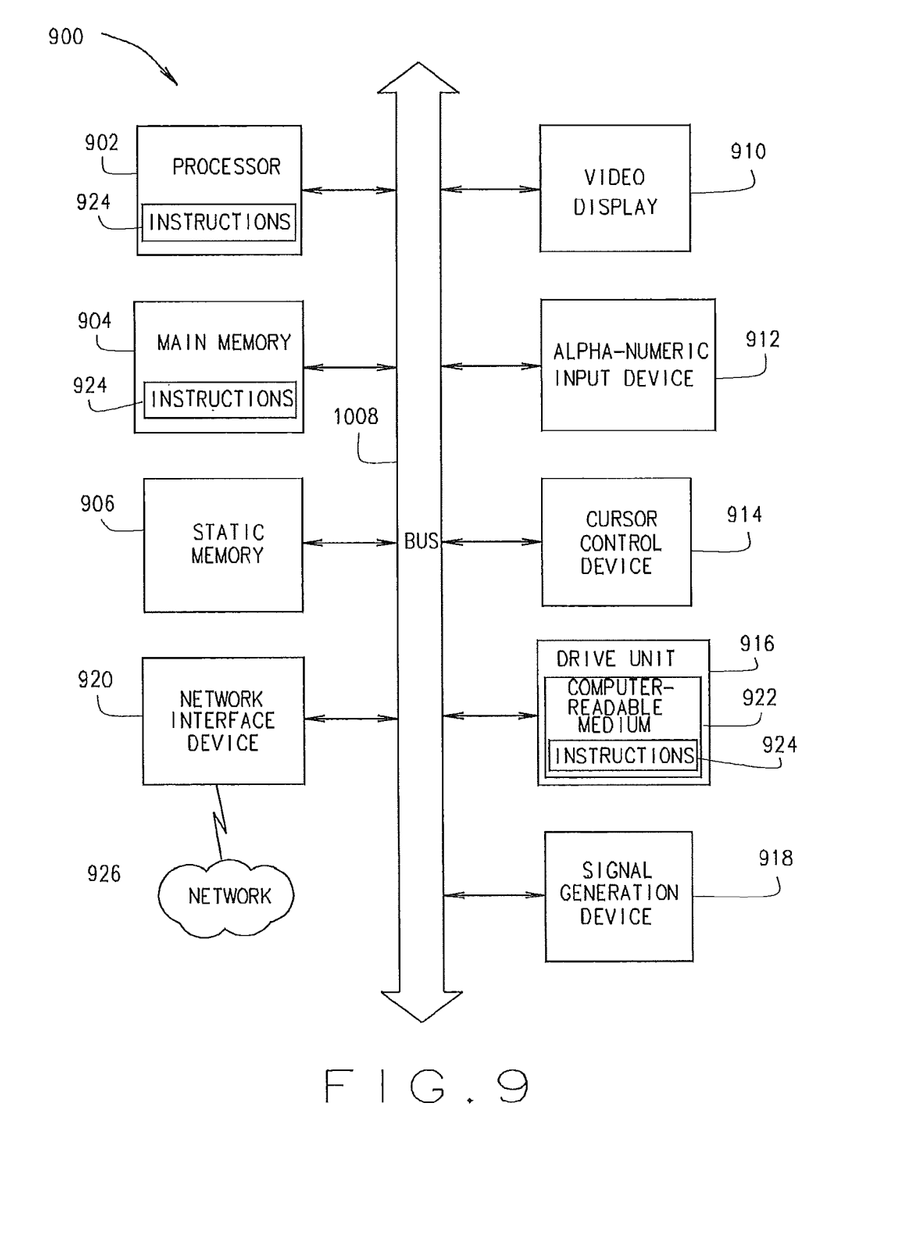
FIG. 9 is a block diagram of a machine in the example form of a computer system within which a set of instructions for causing the machine to perform any one or more of the methodologies discussed herein may be executed or stored.

FIG. 9 shows a block diagram of a machine in the example form of a computer system 900 within which a set of instructions may be executed causing the machine to perform any one or more of the methods, processes, operations, or methodologies discussed herein. The devices 102, 106, 122-144 may include the functionality of the one or more computer systems 900.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (e.g., a central processing unit (CPU) a graphics processing unit (GPU) or both), a main memory 904 and a static memory 906, which communicate with each other via a bus 908. The computer system 900 further includes a video display unit 910 (e.g., a liquid crystal display (LCD) or a cathode ray tube (CRT)). The computer system 900 also includes an alphanumeric input device 912 (e.g., a keyboard), a cursor control device 914 (e.g., a mouse), a drive unit 916, a signal generation device 918 (e.g., a speaker) and a network interface device 920.

The drive unit 916 includes a computer-readable medium 922 on which is stored one or more sets of instructions (e.g., software 924) embodying any one or more of the methodologies or functions described herein. The software 924 may also reside, completely or at least partially, within the main memory 904 and/or within the processor 902 during execution thereof by the computer system 900, the main memory 904 and the processor 902 also constituting computer-readable media.

The software 924 may further be transmitted or received over a network 926 via the network interface device 920.

While the computer-readable medium 922 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a system is provided with a conveyor section, a staging area, and a packing area. The conveyor section is adapted to direct order components to a staging bin. The staging area is adjacent the conveyor section, and includes staging bins which may hold order components and distribute such components to a shuttle. The shuttle may release the components to the packing area when the packing area is ready, and may then receive another set of components from a staging bin to stage the next order. A worker in the packing area may scan the components as the components are placed in a wrap seal pocket to verify the components.

The present disclosure makes reference to a robot and words of similar import. A robot can be a machine capable of carrying out a complex series of actions automatically. These complex series of actions may include picking up, orientating, positioning and/or releasing a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, e.g., a robot may move location, have an articulated arm, have grasping structures that replicate like fingers and do not damage containers, and the like.

Thus, methods and systems for unit-of-use packing have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A system comprising:
   a staging area including:
      a plurality of staging bins, and
      a shuttle moveable along the plurality of staging bins,
      wherein a staging bin of the plurality of staging bins is configured to selectively retain a component of an order therein, and configured to selectively release the component to the shuttle; and
   a packing area including:
      a slide,
      a scanner, and
      a wrap seal conveyor,
      wherein the shuttle is configured to release the component onto the slide, and
      wherein the scanner is operable to scan and verify the component during placement of the component onto the wrap seal conveyor.

2. The system of claim 1, wherein the shuttle is moveable beneath the plurality of staging bins.

3. The system of claim 1, wherein the staging bin includes a selectively openable door for selectively retaining the component of the order therein.

4. The system of claim 3, wherein the shuttle is positionable proximate the door in the staging bin to receive the component of the order from the staging bin.

5. The system of claim 1, further comprising:
   a staging conveyor leading to the staging bin;
   a holding bin associated with the staging conveyor; and
   a feed conveyor for transporting the components of the order to the holding bin.

6. The system of claim 5, wherein the staging conveyor is a Z-conveyor.

7. The system of claim 5, wherein the holding bin includes a selectively openable door to allow the component of the order to be transported out of the holding bin on its respective staging conveyor.

8. The system of claim 5, wherein the feed conveyor includes a drop door, the drop door being associated with the holding bin.

9. The system of claim 8, wherein the drop door is a bomb bay style door, and wherein the holding bin prevents the component of the order dropped through the bomb bay style door in the feed conveyor from bouncing into a different holding bin associated with the staging conveyor.

10. The system of claim 1, wherein the shuttle moves along a track positioned along the plurality of staging bins.

11. The system of claim 1 wherein the shuttle includes a selectively openable door for releasing the component of the order onto the slide.

12. A method comprising:
    depositing a container associated with a prescription order into a holding bin;
    transporting the container from the holding bin on a staging conveyor;
    depositing the container from the staging conveyor into a staging bin;
    instructing a shuttle to move to a position adjacent the staging bin to receive the container;
    opening a door of the staging bin to release the container from the staging bin to the shuttle;
    instructing the shuttle to move to a slide; and
    depositing the container from the shuttle onto the slide, causing the container to slide down the slide to a gathering area for packing.

13. The method of claim 12, further comprising:
    instructing the shuttle to move to a position adjacent a next staging bin to receive a next prescription order;
    opening a door of the next staging bin to release the next prescription order to the shuttle;
    instructing the shuttle to move to the slide to await completion of packing of the container.

14. The method of claim 12, further comprising:
    transporting the container to the holding bin via a feed conveyor,
    wherein depositing the container into the holding bin occurs by dropping the container from the feed conveyor through a bomb bay style drop door.

15. The method of claim 12, further comprising:
    determining that the container includes all container components of a prescription order based on a scan of the container, said determination occurring in a control unit; and
    instructing a worker to package the container for shipment based on the determination.

16. The method of claim 12, further comprising:
    determining that the container does not include all container components of a prescription order based on a scan of the container, said determination occurring in a control unit; and
    instructing a worker to reject the container based on the determination.

17. The method of claim 12, wherein the position adjacent the staging bin is beneath the staging bin.

18. The method of claim 12, further comprising:
    opening a door of the holding bin to allow the container to exit the holding bin.

19. The method of claim 12, wherein depositing the container from the shuttle onto the slide comprises:
    opening a door of the shuttle to release the container onto the slide.

20. The method of claim 12, wherein the container including an order comprises an order of a prescription pharmaceutical.

21. The method of claim 12, further comprising:
    scanning the container to confirm that all container components of a prescription order are present, the container components including the component and an additional component.

22. A method comprising:
    depositing a container associated with a prescription order into a particular holding bin of a plurality of holding bins;
    determining that a staging bin associated the holding bin is empty, wherein the determination occurs in a control unit;
    advancing a conveyor between the holding bin and a staging bin to transport the container to the staging bin;
    depositing the container from the conveyor into the staging bin;
    moving a shuttle to a position adjacent the staging bin to receive the container;
    opening a door of the staging bin to release the container from the staging bin to the shuttle to stage the order;
    moving the shuttle to a slide after receipt of the container from the staging bin;
    depositing the container from the shuttle onto the slide, causing the at least one container to slide down the slide to a gathering area;
    moving the shuttle to a position proximate another staging bin to stage a next order; and
    scanning the container to confirm that all containers of the order are present.

* * * * *